United States Patent
Bringhen et al.

(10) Patent No.: US 10,815,177 B2
(45) Date of Patent: Oct. 27, 2020

(54) PROCESS OF MAKING ORGANIC COMPOUNDS

(71) Applicant: GIVAUDAN SA, Vernier (CH)

(72) Inventors: Alain Bringhen, Choulex (CH); Jacques Membrez, La Tour-de-Peilz (CH)

(73) Assignee: GIVAUDAN SA, Vernier (CH)

( * ) Notice: Subject to any disclaimer, the term of this patent is extended or adjusted under 35 U.S.C. 154(b) by 0 days.

(21) Appl. No.: 16/646,446

(22) PCT Filed: Oct. 30, 2018

(86) PCT No.: PCT/EP2018/079627
§ 371 (c)(1),
(2) Date: Mar. 11, 2020

(87) PCT Pub. No.: WO2019/086404
PCT Pub. Date: May 9, 2019

(65) Prior Publication Data
US 2020/0270192 A1  Aug. 27, 2020

(30) Foreign Application Priority Data
Oct. 31, 2017  (EP) ..................... 17199319

(51) Int. Cl.
C07C 29/80   (2006.01)
C12P 17/04   (2006.01)
C07C 33/02   (2006.01)

(52) U.S. Cl.
CPC .............. *C07C 29/80* (2013.01); *C12P 17/04* (2013.01); *C07C 33/02* (2013.01); *C12Y 504/99017* (2013.01)

(58) Field of Classification Search
CPC ......... C07C 29/80; C07C 33/02; C12P 17/04; C12Y 504/99017
See application file for complete search history.

(56) References Cited

U.S. PATENT DOCUMENTS

2013/0273619 A1   10/2013   Bonnekessel et al.

FOREIGN PATENT DOCUMENTS

| WO | 99363379 A1 | 7/1999 |
| WO | 2015059293 A1 | 4/2015 |
| WO | 2016170099 A1 | 10/2016 |
| WO | 2016170106 A1 | 10/2016 |

OTHER PUBLICATIONS

EP Search Report for corresponding application EP17199319.3 dated Apr. 30, 2018.
International Search Report and Written Opinion of the International Searching Authority for corresponding application PCT/EP2018/079627 dated Jan. 28, 2019.
K. Ishihara et al: "Onantio- and Diastereoselective Stepwise cyclisation . . . "; JACS, American Chemical Soc.; vol. 124, No. 14, Mar. 16, 2002, p. 3647-3655.

*Primary Examiner* — Jafar F Parsa
(74) *Attorney, Agent, or Firm* — Norris McLaughlin PA

(57) ABSTRACT

A process of purification of a homoallylic alcohol by distillation in the presence of a base, wherein the homoallylic alcohol is E,E-homofarnesol.

14 Claims, No Drawings

PROCESS OF MAKING ORGANIC COMPOUNDS

This is an application filed under 35 USC 371 based on PCT/EP2018/079627, filed 30 Oct. 2018, which in turn is based on EP 17199319.9 filed 31 Oct. 2017. The present application claims the full priority benefit of these prior applications and herein incorporates by reference the full disclosures of these prior applications.

FIELD

The present invention is concerned with a process of purifying homoallylic alcohols.

BACKGROUND OF THE INVENTION

Homoallylic alcohols are valuable compounds for synthetic chemists. For example, they are useful intermediates in the preparation of flavour and fragrance ingredients.

The homoallylic alcohol E,E-homofarnesol ((3E,7E)-4,8,12-Trimethyltrideca-3,7,11-trien-1-ol) (disclosed for example in US2013/0273619A1 or by Kocienski et al (J. Org. Chem. 54(5), 1215-1217, 1989) is particularly useful in the fragrance field as a substrate, which can be biocatalytically converted to the valuable fragrance ingredient (-)-Ambrox using Squalene Hopene Cyclase. As a substrate in a biocatalytic process, it is imperative that it is prepared and isolated with a very high degree of purity. Distillation is the purification method of choice.

On industrial scale, the E,E-homofarnesol needs to be prepared and also purified in a cost efficient way, and for industrial quantities.

Applicant found, however, when the reaction mixture of E,E-homofarnesol was purified by distillation at elevated temperature, side products were formed in about 5 to 15% by GC in the distillate head fractions, diminishing the yield and/or quality of the desired E,E-homofarnesol.

There remains a need to provide a simple and cost efficient process of purifying homoallylic alcohols in general, and the homoallylic alcohol E,E-homofarnesol in particular.

SUMMARY OF THE INVENTION

Surprisingly, applicant found that by the addition of a base to a crude reaction mixture containing said homoallylic alcohol in a distillation apparatus it was possible to prevent degradation of the homoallylic alcohol, and to purify and recover it in high yield.

In a first aspect of the invention, there is provided a method of purification of a homoallylic alcohol by distillation in the presence of a base.

In a second aspect of the invention there is provided a method of preparing (-)-Ambrox, said method comprising the step of isolating and purifying the homoallylic alcohol E,E-homofarnesol from a reaction mixture by distillation in the presence of a base, and converting the purified E,E-homofarnesol to (-)-Ambrox in a biocatalytic process using Squalene Hopene Cyclase.

In an embodiment of any aspects of the invention, the homoallylic alcohol is E,E-homofarnesol.

In an embodiment of any aspects of the invention, the base has a pKa of at least 7 or higher, preferably of least 9.

In an embodiment of any aspects of the invention the base is an amine.

In an embodiment of any aspects of the invention the base is a secondary or tertiary amine.

In an embodiment of any aspects of the invention the base has a high-boiling point of at least 300° C.

In an embodiment of any aspects of the invention, the base is selected from the group consisting of didecylmethylamine and tridodecylamine.

DETAILED DESCRIPTION OF THE INVENTION

The invention is based on the surprising discovery that the homoallylic alcohol E,E-homofarnesol is thermally labile and degrades at temperatures above 130° C. The formation of a side product, not present in the reaction mixture or in the pre-distilled homoallylic alcohol, takes place at elevated temperature. The side product is formed in significant amounts.

The side product formed during the distillation step was identified to be a tetrahydrofuran derivative that results from the cyclisation of homofarnesol

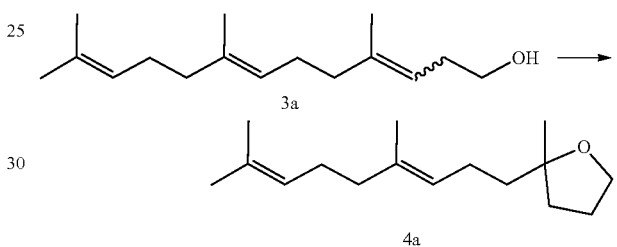

The wavy bond in formula 3a is depicting the unspecified configuration of the adjacent double bond, which is either in E or in Z-configuration, or the compound of formula 3a is present as E/Z-mixture.

It was found that during purification of E,E-homofarnesol by distillation, the formation of tetrahydrofuran derivative 4a can be entirely suppressed by distilling the reaction mixture in the presence of a base.

The purified E,E-homofarnesol can be further converted to (-)-Ambrox in a biocatalytic process using Squalene Hopene Cyclase, as described in WO2016170106 and WO2016170099, which are hereby incorporated by reference.

To prevent or at least significantly reduce the formation of the undesired side product during the distillation of the homoallylic alcohol, the base should be present in 0.1-6% by weight of the reaction mixture, preferably in 1-5% by weight of the reaction mixture, more preferably in 3% by weight of the reaction mixture.

In one aspect of the invention, the base has a $pk_A$ value of at least 7 or higher, preferably of least 9.

In an embodiment of the invention, the base is provided in liquid form.

On an industrial scale, the addition of a base in liquid form is preferred, because it allows for an easier handling and is therefore more suitable. However, alternatively, a base in solid form can also be used.

In one aspect of the invention, the base is an amine. The variety of available amines is large and requires no further elaboration here. Furthermore, other bases might be used in the context of the invention.

In a further aspect of the invention, the base has a boiling point of at least 300° C., preferably a boiling point of at least 350° C.

Advantageously, the base has a boiling point which prevents co-distillation with the homoalyllic alcohol. The base with a sufficiently high boiling point remains in the residue of the reaction mixture in the still pot. Therefore, it has not to be separated from the desired product after distillation, for example by additional washing steps that would add to the overall costs of the process.

In case of E,E-homofarnesol that is further converted in a biocatalytical process, the absence of the base in the purified homoallylic alcohol is of particular importance, to allow for an efficient transformation to (−)-Ambrox using Squalene Hopene Cyclase.

However, bases with lower boiling points can also be useful to prevent formation of the undesired new product. In case the base will be present in the homoallylic alcohol after distillation, a washing procedure can be applied. Such a washing step can be carried out with diluted aqueous acid.

In one aspect of the invention, the base is an amine selected from the group consisting of didecylmethylamine and tridodecylamine. These two bases can prevent formation of undesired new product, they have relatively high boiling points so that they remain in the still pot and they are attractive from economic point of view, as their prices are relatively low.

The invention is now further described with reference to the following non-limiting examples. These examples are for the purpose of illustration only and it is understood that variations and modifications can be made by one skilled in the art.

EXAMPLES

Example 1: Distillation of Crude Homofarnesol 3a Before and after Addition of 3% Triethanolamine

| Fraction No. | GC Analysis [%] | | P [mbar] | T[° C.] | |
|---|---|---|---|---|---|
| | (Z + E) − 3a | 4a | | vapour | still pot |
| 1 | 0.0 | 0.0 | 0.7 | 91 | 130 |
| 2 | 3.3 | 0.0 | 0.7 | 92 | 133 |
| 3 | 45.7 | 9.1 | 0.6 | 94 | 139 |
| 4 | 83.7 | 12.2 | 0.6 | 111 | 149 |
| 5 | 91.5 | 8.3 | 0.6 | 113 | 153 |
| 6 | 90.8 | 8.4 | 0.6 | 113 | 155 |
| 7 | 90.2 | 8.5 | 0.6 | 113 | 155 |
| 8 | 89.2 | 9.1 | 0.6 | 113 | 155 |
| 9 | 83.8 | 12.8 | 0.6 | 113 | 155 |
| Distillation stop, addition of 3%w triethanolamine | | | | | |
| 10 | 80.6 | 15.4 | 0.6 | 112 | 157 |
| 11 | 94.1 | 2.1 | 0.6 | 113 | 157 |
| 12 | 96.9 | 0.4 | 0.6 | 113 | 157 |
| 13 | 97.3 | 0.0 | 0.6 | 113 | 158 |
| 14 | 97.0 | 0.0 | 0.6 | 113 | 164 |
| 15 | 96.9 | 0.0 | 0.6 | 114 | 168 |
| 16 | 95.8 | 0.0 | 0.6 | 117 | 178 |
| 17 | 94.7 | 0.0 | 0.6 | 60 | 190 |

When distillation of crude reaction mixture of homofarnesol 3a is performed without addition of a base, new product 4a is formed in ca. 10% by weight (entries 1-9). By addition of triethanolamine the formation of 4a is suppressed, and 3a can be obtained in higher yield.

Example 2: Distillation of Crude Homofarnesol 3a Containing 3% w Tridodecylamine

| Fraction No. | GC Analysis [%] | | P [mbar] | T[° C.] | |
|---|---|---|---|---|---|
| | (Z + E) − 3a | 4a | | vapour | still pot |
| 1 | 2.4 | 0.4 | 2 | 86 | 150 |
| 2 | 10.8 | 0.8 | 2 | 111 | 168 |
| 3 | 44.1 | 1.1 | 2 | 126 | 170 |
| 4 | 84.4 | 0.5 | 2 | 129 | 170 |
| 5 | 91.4 | 0.1 | 2 | 129 | 170 |
| 6 | 95.9 | 0.0 | 2 | 130 | 171 |
| 7 | 96.2 | 0.0 | 2 | 130 | 171 |
| 8 | 97.6 | 0.0 | 2 | 130 | 171 |
| 9 | 97.5 | 0.0 | 2 | 130 | 171 |
| 10 | 97.8 | 0.0 | 2 | 130 | 171 |
| 11 | 97.0 | 0.0 | 2 | 130 | 185 |
| 12 | 95.9 | 0.0 | 2 | 60 | 190 |

The addition of 3% w tridodecylamine to the crude reaction mixture of homofarnesol prevents the formation of new product 4a during distillation at elevated temperature.

Example 3: Stability of Reaction Mixture

The crude reaction mixture 3a (purity of 88.3%, E/Z ratio of 79:21, containing 0.3% 4a was heated at 180° C. for 8 hours, and analysed by GC:

| addition of base (3% by weight) | bp of base [° C.] | MW of base [g/mol] | pKa of base | 3a [%] | E/Z ratio 3a | 4a [%] |
|---|---|---|---|---|---|---|
| — | | | | 68.8 | 74.0/26.0 | 13.6 |
| Triethanolamine | 335 | 149 | 7.74 | 88.5 | 78.9/21.1 | 0.4 |
| Didecylmethylamine | 365 | 312 | 9.83 | 86.7 | 79.2/20.8 | 0.4 |
| Tridodecylamine | 504 | 522 | 10.82 | 85.6 | 80.2/19.8 | 0.5 |
| Polyvinylpyrrolidone | — | — | — | 81.4 | 78.7/21.3 | 3.2 |
| Didodecylamine | 426 | 354 | 10.85 | 77.2 | 78.4/21.6 | 3.6 |
| Polyethyleneimine | — | — | — | 73.5 | 79.6/20.4 | 0.0 |
| Potassium carbonate | — | — | 10.25 | 85.6 | 78.9/21.1 | 0.0 |

Different bases have been tested for their suitability to prevent formation of new product 4a during distillation of crude homofarnesol 3a. Furthermore, a suitable base should be able to maintain or improve the E/Z-ratio of the homoallylic alcohol, it should have a boiling point high enough to circumvent co-distillation with the homoallylic alcohol, it is preferably a liquid, allowing easy handling on a production scale and it should have an attractive price.

The best candidates fulfilling the listed criteria are didecylmethylamine and tridodecylamine.

The invention claimed is:

1. A process of purification of a homoallylic alcohol by distillation, wherein the distillation is carried out in the presence of a base, and wherein the homoallylic alcohol is E,E-homofarnesol.

2. The process according to claim 1, wherein the base has a $pk_A$ value of at least 7.

3. The process according to claim 1, wherein the base is provided in liquid form.

4. The process according to claim 1, wherein the base is an amine.

5. The process according to claim 4, wherein the base is an amine with a boiling point of at least 300° C.

6. The process according to claim 4, wherein the base is an amine with a molecular weight of at least 150 g/mol.

7. The process according to claim 4, wherein the base is an amine selected from the group consisting of didecylmethylamine and tridodecylamine.

8. A method of preparing (−)-Ambrox, said method comprising the step of:
    purification of E,E-homofarnesol by distillation according to claim 1, and
    converting the purified E,E-homofarnesol to (−)-Ambrox in a biocatalytic process using Squalene Hopene Cyclase.

9. The process according to claim 2, wherein the base has a $pk_A$ value of at least 9.

10. The process according to claim 2, wherein the base is provided in a liquid form.

11. The process according to claim 2, wherein the base is an amine.

12. The process according to claim 5, wherein the base is an amine with a boiling point of at least 300° C.

13. The process according to claim 4, wherein the base is an amine with a molecular weight of at least 300 g/mol.

14. The process according to claim 13, wherein the base is an amine with a molecular weight of at least 500 g/mol.

* * * * *